United States Patent [19]

Mrozinski et al.

[11] Patent Number: 5,352,513
[45] Date of Patent: Oct. 4, 1994

[54] OIL, WATER AND SWEAT REPELLENT MICROPOROUS MEMBRANE MATERIALS

[75] Inventors: James S. Mrozinski, Oakdale; Harold J. Seppala, St. Paul, both of Minn.

[73] Assignee: Minnesota Mining and Manufacturing Company, St. Paul, Minn.

[21] Appl. No.: 99,177

[22] Filed: Jul. 29, 1993

Related U.S. Application Data

[62] Division of Ser. No. 779,015, Oct. 18, 1991, Pat. No. 5,260,360.

[51] Int. Cl.$^5$ ............................................. B32B 3/26
[52] U.S. Cl. .................. 428/315.5; 428/422; 524/95
[58] Field of Search ............... 428/315.5, 422; 524/95

[56] References Cited

U.S. PATENT DOCUMENTS

| | | | |
|---|---|---|---|
| 3,094,547 | 6/1963 | Heine | 260/461 |
| 3,341,497 | 9/1967 | Sherman | 260/72 |
| 4,194,041 | 3/1980 | Gore et al. | 428/315 |
| 4,443,511 | 4/1984 | Worden et al. | 428/198 |
| 4,539,256 | 9/1985 | Shipman | 428/315.5 |
| 4,609,584 | 9/1986 | Cutler et al. | 428/156 |
| 4,613,544 | 9/1986 | Burleigh | 428/315.5 |
| 4,726,989 | 2/1988 | Mrozinski | 428/315.5 |
| 4,824,718 | 4/1989 | Hwang | 428/284 |
| 4,863,792 | 9/1989 | Mrozinski | 428/315.5 |
| 4,867,881 | 9/1989 | Kinzer | 210/490 |
| 4,877,679 | 10/1989 | Leatherman et al. | 428/224 |
| 4,961,985 | 10/1990 | Henn et al. | 428/461 |
| 5,017,292 | 5/1991 | DiLeo et al. | 210/645 |
| 5,025,052 | 6/1991 | Crater et al. | 524/104 |
| 5,032,450 | 7/1991 | Rechlicz et al. | |

FOREIGN PATENT DOCUMENTS

| | | | |
|---|---|---|---|
| 60-142860 | 7/1985 | Japan | A61M 1/34 |
| 64-22305 | 1/1989 | Japan | B01D 13/00 |
| 1-305001 | 1/1989 | Japan | A01N 3/00 |
| 2-212527 | 8/1990 | Japan | C08K 9/36 |

*Primary Examiner*—Joseph L. Schofer
*Assistant Examiner*—Peter D. Mulcahy
*Attorney, Agent, or Firm*—Gary L. Griswold; Walter N. Kirn; Carole Truesdale

[57] ABSTRACT

The invention discloses an oleophobic, hydrophobic, water repellent, moisture vapor and air permeable, heat sealable, microporous membrane material suitable for garment applications. The membrane material comprises a polyolefin polymer, a processing compound which is miscible with the polymer at its melt temperature but phase separates when the polymer is cooled to or below its melt temperature, and a fluorochemical composition. The membrane material is oriented in at least one direction. The membrane materials retain their repellency and moisture vapor permeable properties for extended periods of time in garment applications which expose the membrane materials to perspiration residues which are known to generally contaminate and ultimately destroy the repellency properties of conventional liquid repellent, moisture vapor permeable treatments.

22 Claims, No Drawings

OIL, WATER AND SWEAT REPELLENT MICROPOROUS MEMBRANE MATERIALS

This is a division of application Ser. No. 07/779,015 filed Oct. 18, 1991, now U.S. Pat. No. 5,260,360.

This invention pertains to oleophobic, water repellent, moisture vapor permeable, heat sealable microporous membrane materials.

BACKGROUND of the INVENTION

Liquid repellent, vapor permeable microporous materials that repel water, oil, and other low surface tension fluids have utility for example, as fabrics for waterproof garments and tents, as breathable liners for gloves and clothes, as breathable backings for diapers and disposable products, and as protective covers for biological indicators. The value of these materials lies in their ability to repel a wide range of fluids while permitting the rapid transfer of water vapor through the material.

Commercially available fabrics which have been treated with hydrophobic liquids or polymeric materials such as silicone or fluorocarbon oils or resins to render the fabrics fluid repellent but moisture vapor permeable are well known. While these materials can provide adequate repellency properties along with good moisture vapor transmission properties, their durability is variable as some of the barrier treatments, particularly on microporous substrates, are subject to failure if rubbed, touched, abraded or otherwise contacted or flexed. Additionally, these materials typically do not show long term retention of their repellency properties in garment applications where they are exposed to perspiration, presumably because the barrier treatments are readily contaminated by perspiration residues.

U.S. Pat. No. 4,194,041 (Gore et al.) is representative of a number of patents which describe coatings or laminates purported to provide waterproof articles which do not leak when touched and are breathable. This patent describes a layered article for use in waterproof garments or tents comprising at least two layers: an interior, continuous hydrophilic layer that readily allows water vapor to diffuse therethrough, prevents the transport of surface active agents and contaminating substances such as those found in perspiration, and is substantially resistant to pressure induced flow of liquid water, and a hydrophobic layer that permits the transmission of water vapor and provides thermal insulating properties even when exposed to rain. The hydrophobic layer is preferably waterproof microporous tetrafluoroethylene (PTFE) or polypropylene, which permits the passage of moisture vapor through the pores thereof. The hydrophilic layer transfers moisture vapor therethrough whereupon it passes through the porous hydrophobic layer. Various means of joining the layers are suggested including the application of hydraulic pressure to force the hydrophilic polymer to penetrate into the surface void spaces of the hydrophobic layer.

U.S. Pat. No. 4,443,511 (Worden et al.) discloses a layered waterproof, breathable and stretchable article for use in, for example, material for protective articles. Also disclosed is a waterproof and breathable elastomeric polytetrafluoroethylene layered article bonded to a stretch fabric. The water proof and breathable elastomeric polytetrafluoroethylene layered article bonded to a stretch fabric is described as durable and possessing a moisture vapor transmission rate exceeding 1000 gms/m$^2$ day.

U.S. Pat. No. 4,613,544 (Burleigh) describes a waterproof, moisture vapor permeable unitary sheet material comprising a microporous polymeric matrix having pores comprising continuous passages extending through its thickness and opening into the opposite surfaces thereof, the passages being sufficiently filled with a moisture vapor permeable, water impermeable, hydrophilic material to prevent the passage of water and other liquids through the unitary sheet material while readily permitting moisture vapor transmission therethrough rendering the sheet material breathable. The unitary sheet is made by causing a liquid composition comprising the hydrophilic material or precursor thereof to flow into the pores of the matrix, then causing the conversion thereof to solid hydrophilic material.

While these materials alleviate some of the problems known to the art, many require lamination to protect the water repellent, moisture vapor permeable material they use in their constructions while others require void filling which can lower the moisture vapor transmission rate of the material and decrease its ability to heat seal. Joining of multiple pieces of these materials in a three dimensional garment presents additional problems in that most of these materials are not readily joined together by any means other than sewing which creates needle holes that must be subsequently sealed with seaming tapes or alternative filling techniques to provide a totally waterproof garment. Also, due to the dense nature of the hydrophilic layer, many of these materials are minimally permeable to air.

U.S. Pat. No. 5,025,052 (Crater et al.) describes fluorochemical oxazolidinone compositions and their use for oil and water repellency in films, fibers, and nonwoven webs.

U.S. Pat. No. 4,539,256 (Shipman) discloses a microporous sheet material formed by liquid-solid phase separation of a crystallizable thermoplastic polymer with a compound which is miscible with the thermoplastic polymer at the melting temperature of the polymer but phase separates on cooling at or below the crystallization temperature of the polymer.

U.S. Pat. No. 4,726,989 (Mrozinski) discloses a microporous material similar to that of Shipman but which also incorporates a nucleating agent.

U.S. Pat. No. 4,867,881 (Kinzer) discloses an oriented microporous film formed by liquid-liquid phase separation of a crystalline thermoplastic polymer and a compatible liquid.

SUMMARY OF THE INVENTION

The present invention relates to liquid repellent, moisture vapor and air permeable, microporous membrane materials which comprise an oleophobic, hydrophobic, moisture vapor and air permeable, sweat contamination resistant, heat sealable, microporous membrane material comprising a crystallizable olefin polymer, a processing compound which is miscible with the olefin polymer at the polymer's melting point but phase separates on cooling to or below the crystallization temperature of the polymer, and a fluorochemical oil and water repellent compound which is generally solid at room temperature, preferably a fluorochemical oxazolidinone compound, said material being oriented in at least one direction.

The microporous membrane materials of the present invention retain their liquid repellency and moisture vapor permeability properties for extended periods even in garment applications which expose the membrane materials to perspiration residues which are known to often contaminate and ultimately destroy repellency properties of most conventional fluid repellent, moisture vapor permeable materials. Surprisingly, the materials of the invention retain this contamination resistance to perspiration despite the presence of an oleophilic processing compound. Further, the microporous membrane materials useful in the invention repel mineral oil even when they contain mineral oil. The microporous membrane materials of the present invention also possess excellent hand, drape and heat sealability.

DETAILED DESCRIPTION

The liquid repellent, moisture vapor and air permeable, microporous membrane materials of the present invention repel aqueous based liquids including a variety of other liquids such as perspiration which contains oil-based components and prevent penetration of the liquids through the thin (5 to 250 microns) microporous membrane, even when the liquid is propelled against the membrane material. The microporous membrane materials, while water repellent, also have very high moisture vapor permeabilities coupled with significant air permeability properties.

Garments comprising the microporous membrane materials of the present invention allow for the transfer of moisture vapor resulting from perspiration through the garment at a rate sufficient to maintain the skin of the wearer in a reasonably dry state under normal use conditions. The microporous membrane materials of the present invention are not subject to contamination by perspiration residues which reduce and ultimately destroy the repellency properties of the material. The membrane materials of the present invention can be used in garment applications without a protective overlayer, such as a hydrophilic, e.g., urethane coating.

The microporous membrane materials of the present invention exhibit durability of their fluid repellency properties when subjected to rubbing, touching, folding, flexing or abrasive contacts. The microporous membrane materials of the present invention also display oleophobic properties, resisting penetration by oils and greases and they are heat sealable. The oleophobicity and heat sealing properties of the membrane materials are most surprising in that the membrane materials contain an oily, oleophilic processing compound which, a priori, one would expect, would promote wetting by other oleophilic materials and which also would inhibit heat sealing.

Transport of a liquid challenge through most porous materials or fabrics occurs because the liquid is able to wet the material. A possible route through the material is for the liquid to initially wet the surface of the material and to subsequently enter the pore openings at the surface of the material followed by a progressive wetting of and travel through the interconnected pores until finally reaching the opposite surface of the material. If the liquid has difficulty wetting the material, liquid penetration into and through the material will, for the most part, be reduced. A similar phenomena occurs in the pores, where reduced wetability, in turn, reduces pore invasion. Generally the greater the numerical difference between the liquid surface tension of the liquid and the surface energy of the porous material (the latter being lower), the less likely the liquid will wet the porous material.

In the present invention, the addition of a fluorochemical to the oleophilic microporous membrane is believed to reduce the surface energy of the membrane despite the presence of the generally oleophilic processing compound. Thereby the numerical difference between the surface energy of the membrane and the surface tension of challenge liquids is increased with the overall result that the microporous membrane containing the fluorochemical is oleophobic despite the presence of the processing compound.

The oleophobic, hydrophobic, moisture vapor permeable, air permeable, heat sealable, microporous membrane materials of the present invention comprise a polymeric microporous membrane having a matrix of pores comprising continuous passages extending through the thickness of the membrane and opening into the opposite surfaces of the membrane. The polymer used to prepare the microporous membrane contains a fluorochemical oxazolidinone which migrates to an air interface, thereby lowering the surface energy of the face of the membrane as well as the walls of the pores in the membrane, thereby enhancing the hydrophobic properties of the microporous membrane as well as rendering the microporous membrane material oleophobic.

The microporous membrane materials of the present invention can be tailored to have moisture vapor permeability rates over a broad range without adversely impacting their water repellencies, but it is preferable to have a moisture vapor transmission rate (MVTR) of at least 700 g/m$^2$/24 hrs. and more preferably a MVTR of at least 1000 g/m$^2$/24 hrs.

The term "water repellent" is used herein to describe microporous membrane materials which are not water wettable and are capable of preventing the passage of liquid water through the membrane material by capillary action under varying ambient atmospheric conditions, including water impinging on the surface of the membrane material.

"Moisture vapor permeable" is used herein to describe microporous membrane materials which readily permit the passage of water vapor through the fabric but which do not allow the passage of liquid water.

The term "hydrophobic" is used herein to describe microporous membrane materials which are not wet by liquid water or aqueous body fluids such as blood, saliva, perspiration and urine, and which are capable of repelling and preventing the passage of liquid water through their structure.

The term "oleophobic" is used herein to describe microporous membrane materials which are not wet by oils, greases or body fluids which contain oily components such as perspiration, and are capable of preventing the passage of oils and greases through their structure.

The term "heat sealable" is used herein to describe microporous membrane materials which can be sealed together using a hot-bar sealer to form a bond having a bond strength of at least 0.1 kg/cm width.

The present invention will be described utilizing the fluorochemical oxazolidinone but it will be recognized by those skilled in the art that other generally solid fluorochemicals can be used.

The oleophobic, hydrophobic, moisture permeable, air permeable, heat sealable, microporous membrane materials of the present invention can preferably be made by the following steps: (a) melt blending into a homogeneous blend, a mixture comprising about 40 to about 80 parts by weight of a crystallizable olefin polymer, about 20 to 60 parts by weight of a processing compound which will dissolve the polymer at the polymer's melting temperature but which will also phase separate from the polymer on cooling to a temperature at or below the crystallization temperature of the polymer, and 0.3 to 7 parts by weight of the fluorochemical oxazolidinone; (b) forming a film from the melt blended mixture; (c) cooling the film to a temperature at which phase separation occurs between the compound and the polymer, thereby creating a phase separated film comprising an aggregate of a first phase comprising particles of crystalline olefin polymer in a second phase comprising the processing compound and the fluorochemical oxazolidinone, with adjacent olefin polymer particles being distinct but having a plurality of zones of continuity; and (d) stretching the phase separated film in at least one direction to separate adjacent particles of olefin polymer from one another to provide a network of inter-connected micropores and to permanently attenuate the olefin polymer in the zones of continuity to form fibrils. Optionally a nucleating agent may also be added in step (a). Such methods are described, for example, in U.S. Pat. No. 4,539,256 (Shipman), U.S. Pat. No. 4,726,989 (Mrozinski) and U.S. Pat. No. 4,863,792 (Mrozinski), which are incorporated herein by reference.

Alternatively, as a subsequent dimension of this invention, if a large weight percent of a generally solid fluorochemical composition, preferably a fluorochemical oxazolidinone can be tolerated (i.e. >5% by weight), it is possible to topically apply a fluorochemical composition to the microporous membrane material through spray application or dip coating techniques. Examples of membranes which contain the phase separating processing compound that can be topically treated include crystalline polyolefin membranes described, for example, in U.S. Pat. No. 4,539,256 (Shipman), U.S. Pat. No. 4,726,989 (Mrozinski), U.S. Pat. No. 4,863,792 (Mrozinski) and U.S. Pat. No. 4,824,718 (Hwang) each of which is incorporated herein by reference. Further, these fluorochemical compositions can be topically applied to other microporous materials such as stretched polytetrafluoroethylene or particle loaded films which do not contain the processing compound.

The phase separated films typically are solid and generally transparent before stretching and comprise an aggregate of a first phase of particles of olefin polymer in a second phase of the processing compound and the fluorochemical oxazolidinone. The particles may be described as spherulites and aggregates of spherulites of the olefin polymer, with processing compound and the fluorochemical oxazolidinone occupying the space between particles. Adjacent particles of polymer are distinct, but they have a plurality of zones of continuity. That is, the polymer particles are generally substantially, but not totally, surrounded or coated by the processing compound and the fluorochemical oxazolidinone. There are areas of contact between adjacent polymer particles where there is a continuum of polymer from one particle to the next adjacent particle in such zones of continuity.

On stretching, the polymer particles are pulled apart, permanently attenuating the polymer in zones of continuity, thereby forming the fibrils and creating minute voids between coated particles which results in a network of interconnected micropores. Such permanent attenuation also renders the article permanently translucent. On stretching, the processing compound and the fluorochemical oxazolidinone remain coated on or substantially surrounding the surfaces of the resultant fibril/particle matrix. The degree of coating depends on several factors, including, but not limited to, the affinity of the compound and the fluorochemical oxazolidinone for the surface of the polymer particle, whether the compound is liquid or solid, and whether stretching dislodges or disrupts the coating. After the stretching operation, substantially all of the particles appear to be connected by fibrils and are usually at least partially coated. The size of the micropores is easily controlled by varying the degree of stretching, the amount of processing compound employed, melt-quench conditions, and heat stabilization procedures. For the most part, the fibrils do not appear to be broken by stretching, but they are permanently stretched beyond their elastic limit so that they do not elastically recover to their original position when the stretching force is released. As used herein, "stretching" means such stretching beyond the elastic limit so as to introduce permanent set or elongation to the microporous membrane material.

Preferably, the melting and crystallization temperature of an olefin polymer, in the presence of a processing compound, is influenced by both an equilibrium and a dynamic effect. At equilibrium between liquid and crystalline polymer, thermodynamics require that the chemical potentials of the polymer repeating unit in the two phases be equal. The temperature at which this condition is satisfied is referred to as the melting temperature, which depends upon the composition of the liquid phase. The presence of a diluent, e.g., the processing compound, in the liquid phase will lower the chemical potential of the polymer in that phase. Therefore, a lower melting temperature is required to re-establish the condition of equilibrium, resulting in what is known as a melting temperature depression.

The crystallization temperature and melting temperature are equivalent at equilibrium. However, at non-equilibrium conditions, which are normally the case, the crystallization temperature and melting temperature are dependent on the cooling rate and heating rate, respectively. Consequently, the terms "melting temperature" and "crystallization temperature," when used herein, are intended to include the equilibrium effect of the processing compound as well as the dynamic effect of the rate of heating and cooling.

The microporous membrane materials of the present invention have a microporous structure characterized by a multiplicity of spaced, i.e., separated from one another, randomly dispersed, non-uniform shaped, equiaxed particles of olefin polymer connected by fibrils which are intimately surrounded by the processing compound and the fluorochemical oxazolidinone. "Equiaxed" means having approximately equal dimensions in all directions.

While the preferred form of the microporous membrane materials of the present invention is a sheet or film form, other article shapes are contemplated and may be formed. For example, the article may be in the form of a tube or filament or hollow fiber. Other shapes which can be made according to the disclosed process are also intended to be within the scope of the invention.

Nucleating agents as described in U.S. Pat. No. 4,726,989 (Mrozinski) may also be used in the preparation of the microporous membrane materials of the present invention. The use of nucleating agents provides various advantages including lower polymer content and thus higher porosity of the finished article, reduced polymer particle size resulting in more particles and fibrils per unit volume, greater stretchability resulting in longer fibril length, and greatly increased tensile strength of the material.

Crystallizable olefin polymers suitable for use in the preparation of microporous membrane materials of the present invention are melt processable under conventional processing conditions. That is, on heating, they will easily soften and/or melt to permit processing in conventional equipment, such as an extruder, to form a sheet, film, tube, filament or hollow fiber. Upon cooling the melt under controlled conditions, suitable polymers spontaneously form geometrically regular and ordered crystalline structures. Preferred crystallizable olefin polymers for use in the present invention have a high degree of crystallinity and also possess a tensile strength of at least about 70 kg/cm$^2$ (1000 psi).

Examples of commercially available suitable polyolefins include polypropylene, block copolymers or copolymers of ethylene and propylene, or other copolymers, such as polyethylene, polypropylene and polybutylene copolymers which can be used singularly or in a mixture.

Materials suitable as processing compounds for blending with the crystallizable polymer to make the microporous membrane materials of the present invention are liquids or solids which are not solvents for the crystallizable polymer at room temperature. However, at the melt temperature of the crystallizable polymer the compounds become good solvents for the polymer and dissolve it to form a homogeneous solution. The homogeneous solution is extruded through, for example, a film die, and on cooling to or below the crystallization temperature of the crystallizable polymer, the solution phase separates to form a phase separated film. Preferably, these compounds have a boiling point at atmospheric pressure at least as high as the melting temperature of the polymer. However, compounds having lower boiling points may be used in those instances where superatmospheric pressure may be employed to elevate the boiling point of the compound to a temperature at least as high as the melting temperature of the polymer. Generally, suitable compounds have a solubility parameter and a hydrogen bonding parameter within a few units of the values of these same parameters for the polymer.

Some examples of blends of olefin polymers and processing compounds which are useful in preparing microporous materials in accordance with the present invention include: polypropylene with mineral oil, dioctylphthalate, or mineral spirits; and polyethlyene-polypropylene copolymers with mineral oil or mineral spirits. Typical blending ratios are 40 to 80 weight percent polymer and 20 to 60 weight percent blending compound.

A particular combination of polymer and processing compound may include more than one polymer, i.e., a mixture of two or more polymers, e.g., polypropylene and polybutylene, and/or more than one blending compound. Mineral oil and mineral spirits are examples of mixtures of processing compounds, since they are typically blends of hydrocarbon liquids. Similarly, blends of liquids and solids may also serve as the processing compound.

Fluorochemical oxazolidinones suitable for use in the present invention are normally solid, water-insoluble, fluoroaliphatic radical-containing 2-oxazolidinone compounds which have one or more 2-oxazolidinone moieties, at least one of which has a monovalent fluoroaliphatic radical containing at least 3 fully fluorinated terminal carbon atoms bonded to the 5-position carbon atom thereof by an organic linking group, preferably

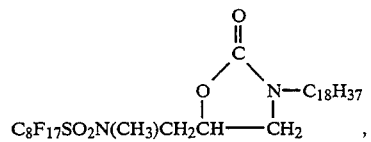

are described in U.S. Pat. No. 5,025,052 (Crater et al.) which is incorporated herein by reference. These oxazolidinone compounds are normally blended in the polymer/processing compound mixture in the ratio of 1 to 5 weight percent. More preferably the fluorochemical oxazolidinone compounds are added to the polymer/processing compound mixture in the ratio of 1 to 2 weight percent. Fluorochemical oxazolidinone compounds can be added to the membranes of the present invention in amounts greater than 5 weight percent (i.e. 10 weight percent), but additions in excess of about 2 weight percent typically do not show any performance advantages.

It is also expected that additional oil and water repellent fluorochemical compositions would provide comparable properties when added during extrusion at the proper extrusion conditions.

Optionally, these compounds, as well as commonly available well-known oil and water repellent fluorochemical compositions, can be topically applied to a microporous membrane material. Typically, topical application of a fluorochemical composition requires a higher weight percent add-on, typically 4 to 15 percent, to achieve comparable water and oil repellency properties as achieved when the fluorochemical oxazolidinone is incorporated in the polymer melt. Additionally, post membrane formation application of the fluorochemical composition requires that the composition be dissolved in a solvent and that the solvent subsequently be removed from the membrane material. The solvent should not be a solvent for the polymer or the processing compound.

Certain conventional additive materials, may also be blended in limited quantities with the olefin polymer. Additive levels should be chosen so as not to interfere with the formation of the microporous membrane material or to result in unwanted exuding of the additive. Such additives may include, for example, dyes, pigments, plasticizers, UV absorbers, antioxidants, bactericides, fungicides, ionizing radiation resistant additives, and the like. Additive levels should typically be less than about 10% of the weight of the polymer component, and preferably be less than about 2% by weight. The microporous membrane materials may also be layered with or laminated to another porous material which does not substantially affect the porosity of the microporous material.

In the following non-limiting examples, all parts and percentages are by weight unless otherwise indicated. In evaluating the materials of the invention and the comparative materials, the following test methods are used.

Porosity

Porosity is measured according to ASTM-D-726-58 Method A and is reported in Gurley Seconds/50 cc.

Bubble Point

Bubble point values represent the largest effective pore size measured in microns according to ASTM-F-316-80 and is reported in microns.

Moisture Vapor Transmission Rate (MVTR)

Moisture vapor transmission rates (MVTR) were made using ASTM E-96-80 Upright Water Method at 70° F., 50% relative humidity and are reported in g/m$^2$/24hr.

Water Repellency Test (WR)

The aqueous stain or water repellency of the materials of the invention is measured using a water/isopropyl alcohol test, and the result is expressed in terms of a water repellency rating of the material. Materials which are penetrated by or resistant only to a 100 percent water/zero percent isopropyl alcohol mixture (the least penetrating of the test mixtures) are given a rating of 0, whereas treated fabrics resistant to zero percent water/100 percent isopropyl alcohol mixture (the most penetrating of the test mixtures) are given a rating of 10. Other intermediate values are determined by use of other water/isopropyl alcohol mixtures, in which the percentage amounts of water and isopropyl alcohol are each multiples of 10. Results are reported as an average of replicate testing. The water repellency rating corresponds to the most penetrating mixture which does not penetrate or wet the fabric after 30 seconds contact.

Oil Repellency Test (OR)

The oil repellency of materials of the invention is measured by the American Association of Textile Chemists and Colorists (AATCC) Standard Test Method No. 118-1983, which test is based on the resistance of treated fabric to penetration by oils of varying surface tensions. Treated fabrics resistant only to Nujol TM, a brand of mineral oil and the least penetrating of the test oils, are given a rating of 1, whereas treated fabrics resistant to heptane (the most penetrating of the test oils) are given a value of 8. Other intermediate values are determined by use of other pure oils or mixtures of oils, as shown in the following table:

| AATCC OIL Repellency Rating Number | Standard Test Liquids Composition |
|---|---|
| 1 | Nujol TM |
| 2 | 65:35 Nujol TM :hexadecane by volume |
| 3 | n-hexadecane |
| 4 | n-tetradecane |
| 5 | n-dodecane |
| 6 | n-decane |
| 7 | n-octane |
| 8 | n-heptane |

The rated oil repellency corresponds to the most penetrating oil (or mixture of oils) which does not penetrate or wet the fabric after 30 seconds contact. Higher numbers indicate better oil repellency.

Sweat Contamination Resistance

Resistance to sweat contamination was measured according to MIL-C-44187B, Mar. 31, 1988, test method 4.5.7 and is reported as being resistant or not resistant.

Heat Seal Bond Strength

Heat seal bond strength was measured by heat sealing two pieces of membrane together on a Sentinal Model 12AS hot bar sealer (Packaging Industries, Inc., Hyannis, Me.) at a temperature of 143° C. (290° F.) for 0.75 seconds at 310 kPa (45 psi) pressure and determining the strength of the bond according to ASTM D751-79 Method A (reported in kilograms per centimeter width).

EXAMPLES

OXAZOLIDINONE PREPARATION

The fluorochemical oxazolidinone (FCO) used in the following examples was similar to those described in U.S. Pat. No. 5,025,052 (Crater et al.) Example 1, except that the alcohol and isocyanate reactants used to prepare the oxazolidinone were $C_8F_{17}SO_2N(CH_3)CH_2CH(CH_2Cl)OH$ and $OCNC_{18}H_{37}$, respectively.

EXAMPLE 1

A 0.05 mm thick sheet of microporous membrane material was prepared using a thermally induced phase separation technique comprising about 65 parts polypropylene (Pp) having a melt flow index of 0.8 dg/min ASTM 1238 (available from Himont Incorporated, Wilmington, Delaware under the trade designation PROFAX 6723) and about 35 parts mineral oil (MO), (available from AMOCO Oil Company under the trade designation AMOCO White Mineral Oil #31 USP Grade). About 1.3 parts fluorocarbon oxazolidinone (FCO) compound and about 0.05 parts Millad 3905 (available from Milliken Chemical under the trade designation Millad 3905) were added to the PP:MO blend. The PP/MO/FCO/MILLAD composition was melt extruded on a twin screw extruder operated at a decreasing temperature profile of 260° to 193° C. through a slip gap sheeting die having an orifice of 30.5×0.05 cm and quenched in a water bath maintained at 54° C. The phase separated film was continuously oriented or stretched in the machine direction (length) to a 1.25:1 stretch ratio at 50° C. and followed by a continuous orientation or stretch in the cross machine direction (width) in a tenter oven to a 2.25:1 stretch ratio at 83° C. and then heat annealed at 121° C. Membrane characterization data are reported in Table I.

COMPARATIVE EXAMPLE C1

A 0.04 mm thick sheet of microporous membrane material was prepared by using the same process and polypropylene/mineral oil/nucleating agent materials as Example 1, but with no FCO compound to provide a comparative membrane material. Membrane characterization data is reported in Table I.

EXAMPLE 2

A 0.036 mm thick sheet of microporous membrane material was prepared from the same PP/MO materials used in Example 1, but at a 68:32 (PP:MO) weight ratio to which about 0.05 parts Millad 3905 and 0.7 parts FCO were added. The PP/MO/FCO/Millad composition was melt extruded as Example 1 but it was quenched in a water bath at 60° C. and biaxially oriented 1.25×1.75 (MD×TD). Membrane characterization data is reported in Table I.

EXAMPLE 3

A 0.08 mm thick sheet of microporous membrane material was prepared from the same PP and mineral oil used in Example 1, but at a 55:45 PP:MO weight ratio. About 5.5 parts FCO were added to the mixture. The PP/MO/FCO was melt extruded as Example 1, but was biaxially stretched 1.25×1.75 (MD×TD). Membrane characterization data is reported in Table I.

EXAMPLE 4

A 0.09 mm thick sheet of microporous membrane material was prepared from about 54 parts polypropylene/polyethylene copolymer having a melt flow index of 0.4 dg/min ASTM 1238 (available from Himont Incorporated, Wilmington, DE under the trade designation PRO-FAX 7823) and about 46 parts mineral oil to which about 1.1 parts FCO was added. The PP-PE copolymer/MO/FCO was melt extruded at process conditions similar to Example 1 except at a throughput rate of 11.35 Kg/hour and a stretch ratio of 1.25×1.75 (MD×TD). Membrane characterization data is reported in Table I.

EXAMPLE 5

A 0.07 mm thick sheet of microporous membrane material was prepared from the same polypropylene and mineral oil used in Example 1, but at a 40:60 weight ratio to which about 0.8 parts FCO were added. The PP/MO/FCO was melt extruded at conditions similar to Example 1 except it was quenched in a water bath maintained at 47° C. and biaxially stretched 1.25 by 1.75. Membrane characterization data is reported in Table I.

EXAMPLE 6

A 0.05 thick sheet of microporous membrane material was prepared from the same PP/MO materials used in Example 1, but at an 75:25 PP:MO weight ratio to which about 1.9 parts FCO were added. The PP/MO/FCO composition was melt extruded on a 25 mm twin screw extruder operated at a decreasing temperature profile of 260° to 230° C. through a 7.62 cm circular blown film die. The blown film was length stretched 1.3:1 at 70° C. Membrane characterization data is reported in Table I.

COMPARATIVE EXAMPLE C2

A sheet of microporous membrane material was prepared by using the same process and polypropylene/mineral oil/nucleating agent materials as Example 2, but with no oxazolidinone compound to provide a comparative membrane material. Membrane characterization data is reported in Table I.

EXAMPLE 7

A sheet of microporous membrane material was prepared by using the same process and polypropylene/mineral oil/nucleating agent materials as Example 2, except that 1.1 parts FCO was added to the mixture. Membrane characterization data is reported in Table I.

TABLE I

EXTRUSION INCORPORATION MEMBRANE CHARACTERIZATION DATA

| Ex. No. | Porosity (Gurley Sec) | Pore Size (μm) | MVTR (g/m²/ 24 hr) | Water Repellency | Oil Repellency | Resistance to Sweat Contamination | Heat Seal Bond (kg/cm) |
|---|---|---|---|---|---|---|---|
| 1 | 370 | 0.130 | 987 | 9 | 2 | Yes | 0.77 |
| C1 | 226 | 0.192 | 931 | 2 | 0 | No | 0.93 |
| 2 | 62 | 0.380 | 1027 | 8 | 1 | Yes | 0.72 |
| 3 | 96 | 0.270 | 1030 | 9 | 2 | Yes | 0.79 |
| 4 | 205 | 0.380 | 904 | 9 | 2 | Yes | 0.68 |
| 5 | 110 | 0.430 | 793 | 9 | 1 | Yes | 0.29 |
| 6 | 515 | 0.460 | 435 | 6 | 2 | Yes | 0.45 |
| C2 | 192 | — | 986 | 2 | 1 | No | 0.61 |
| 7 | 98 | — | 1072 | 9 | 2 | Yes | 0.59 |

EXAMPLE 8

A 0.05 mm thick sheet of microporous membrane material was prepared using a blend of 58 parts polypropylene (available from Himont Incorporated, Wilmington, Del. under the trade designation PRO-FAX 6723) 15 parts poly(ethylene/butylene) copolymer (available from Shell Chemical under the designation DP 8510) 25.5 parts of a red pigmented polypropylene (available from Spectrum, formerly C. B. Edwards, under the designation CBE 34227 P Red), 1.5 parts FCO which was melt blended with 35 parts mineral oil on a 25 mm twin screw extruder operating under conditions similar to those described in Example 6. The polymer/pigment/FCO/MO blend was extruded through a 7.62 cm circular blown film die and was subsequently length oriented 2:1 at 60° C. The porosity was 170 Gurley sec and the pore size was 0.30 μm.

EXAMPLE 9

A 0.04 mm thick sheet of air permeable, perspiration repellent microporous membrane material was prepared using the same materials and process as Example 1, except a blue PP pigment (available from PMS Consolidated, Somerset, N.J. under the trade designation BLUE P293C) was added to color the existing material. The blend ratio of materials was 63.7/1.3/2.0/33.0, PP/FCO/BLUE/MO. The process differences included casting the molten blend maintained at 205° C. from a slip gap sheeting die with a 38.1×0.05 cm orifice onto a smooth steel casting wheel maintained at 66° C. The membrane was then continuously length direction stretched at a ratio of 1.75:1 and continuously width direction stretched 2:1 at 93° C. and heat annealed at 130° C. The porosity was 200 Gurley sec., the pore size 0.28 μm, the MVTR 6954 g/m²/24 hr at 100° F. and 20% relative humidity and the membrane was resistant to sweat contamination.

Fluorochemical oxazolidinone compounds can also be topically applied to microporous membrane materials to produce hydrophobic, oleophobic, sweat contamination resistant materials. Generally speaking, a significantly higher add-on of fluorochemical oxazolidinone compound was required to produce repellencies (both oil and water) and resistance to sweat contamination comparable to that obtained with extrusion incorporation of the oxazolidinone.

EXAMPLE 10

A sheet of microporous membrane material was prepared by using the same process and polypropylene/ mineral oil/nucleating agent materials as Comparative Example C2 and the FCO was applied to the membrane material by dipping the membrane into a 5% solids (w/w) solution of the FCO in isopropyl alcohol (IPA), which was maintained at 66° C., for 3 seconds. The microporous membrane material was then placed into a circulating air oven maintained at 100° C. to evaporate the solvent, leaving the oxazolidinone intimately surrounding the membrane interstices. The FCO add-on was approximately 7% by weight. The membrane was resistant to sweat contamination.

EXAMPLE 11

A sheet of microporous membrane material of Comparative Example I was dipped into a 5% solids (w/w) solution of FCO in IPA, which was maintained at 66° C., for 3 seconds and dried as in Example 10. The FCO add on was approximately 7.0% by weight. The membrane was resistant to sweat contamination.

EXAMPLE 12

A sheet of microporous membrane material of Comparative Example 1 was dipped in a 4% solids (w/w) solution of FCO in IPA which was maintained at 70° C. for 3 seconds and dried in a circulating air oven at 80° C. for two minutes. The treated material was tested for oil repellency. The oil repellency value was 2.

EXAMPLE 13

A sheet of microporous membrane material of Comparative Example 1 was dipped in a 4% solids solution of fluorochemical polymer in a 50/50 water/IPA mixture. The fluorochemical was prepared as in Example 1 of U.S. Pat. No. 4,579,924 except that 75.5 parts $C_8F_{17}SO_2N(CH_3)C_2H_4OCOCH=CH_2$, 17.3 parts $C_2H_5OC_2H_4OCOCH=CH_2$, 2.5 parts

and 4.5 parts $CH_2=C(CH_3)COOC_2H_4N^+(CH_3)_3Cl^-$ were polymerized. The membrane material was dried at 80° C. for two minutes. The treated material was tested for oil repellency. The oil repellency value was 2.

EXAMPLE 14

A sheet of microporous membrane material of Comparative Example 1 was dipped in a 4% solids solution of a fluorochemical composition in a 50/50 water/IPA mixture maintained at room temperature for 3 seconds. The fluorochemical was prepared as in U.S. Pat. No. 3,094,547 (Heine) using 29 parts $[C_8F_{17}SO_2N(CH_2CH_3)C_2H_4O]_2POONH_4$, 5 parts $C_8F_{17}SO_2N(CH_2CH_3)C_2H_4OPO(ONH_4)_2$ and 0.7 parts $[CSF_{17}SO_2N(CH_2CH_3)C_2H_4O]_3PO$, the latter two materials being by-product materials. The membrane material was dried at 80° C. for two minutes. The treated material was tested for oil repellency. The oil repellency value was 2.

EXAMPLE 15

A sheet of microporous membrane material of Comparative Example 1 was dipped in a 4% solids solution of fluorochemical polypher in IPA. The fluorochemical was prepared as in U.S. Pat. No. 3,341,497 (Sherman et al.), Examples VI to VIII, except the components were 50 parts octadecyl methacrylate and 50 parts N-ethyl perfluorooctanesulfon-amidoethyl methacrylate. The membrane material was dried at 80° C. for two minutes. The treated material was tested for oil repellency. The oil repellency value was 2.

EXAMPLE 16

A sheet of microporous membrane material of Comparative Example 1 was dipped in a 4% solids solution of fluorochemical polymer in a 95/5 ethyl acetate/heptane mixture maintained at room temperature for 3 seconds. The fluorochemical was prepared as in U.S. Pat. No. 3,341,497 (Sherman et al.) Examples VI to VIII, except the components were 35 parts octadecyl methacrylate and 65 parts N-ethyl perfluorooctanesulfonamidoethyl methacrylate. The membrane material was dried at 80° C. for two minutes. The treated material was tested for oil repellency. The oil repellency value was 3.

EXAMPLE 17

A 0.03 mm thick sheet of microporous membrane material was prepared for lamination to a polypropylene spunbonded nonwoven using the same materials as Example 9, except a polybutylene (PB) copolymer (available from Shell Chemical Company under the trade designation Pp was added to make a blend ratio of 61.8/1.3/2.0/5.0/30, PP/FCO/BLUE/PB/MO.

This composition was melt extruded through a circular blown film die having a diameter of 30.5 cm and an orifice of 0.05 cm to form a 2 mil film with a lay flat width of 91 cm. The membrane was continuously length stretched to a 1.6:1 stretch ratio at 38° C. and heat annealed at 119° C. The membrane was then thermally bonded to a 1.0 ounce polypropylene spunbond nonwoven (trademark "Celestra", supplied by Fiberweb). The laminating process included running the membrane and nonwoven between a smooth roll and a heated point-bonding roll (approximately 15 percent point contact). The heat roll was set at 270° F. The pressure applied to the materials was approximately 250 pounds per lineal inch. Membrane data is set forth in Table II.

EXAMPLE 18

The membrane of Example 17 was also adhesively bonded to a similar 1.0 ounce PP spunbonded nonwoven. The adhesive used was a polybutylene resin made by Shell, identified as DP9891D Duraflex, spray applied in a random pattern. The adhesive weight applied was approximately 2 g/m². Membrane data is set forth in Table II.

TABLE II

| Ex. No. | CALIPER (mm) | % FCO | POROSITY (sec/50 cc) | BUBBLE POINT (μm) | MVTR (g/m²/24 hr at 100° F., 20% rh) |
| --- | --- | --- | --- | --- | --- |
| 17 | 0.03 | 1.3 | 221 | 0.40 | — |
| 18 | 0.03 | 1.3 | 295 | 0.32 | 5151 |

What is claimed is:

1. A layered structure comprising a microporous membrane material which comprises a crystallizable olefin polymer, a processing compound which is miscible with the olefin polymer at the polymer's melting point but phase separates on cooling to or below the olefin crystallization temperature of the polymer, the blending ratio of polyolefin to processing compound being in the range of about 40:60 to 80:20, and a fluorochemical oxazolidinone compound, said material being oriented in at least one direction and at least one other porous material which does not substantially affect the porosity of the microporous material.

2. A laminated structure comprising a microporous membrane material which comprises a crystallizable olefin polymer, a processing compound which is miscible with the olefin polymer at the polymer's melting point but phase separates on cooling to or below the olefin crystallization temperature of the polymer, the blending ratio of polyolefin to processing compound being in the range of about 40:60 to 80:20, and a fluorochemical oxazolidinone compound, said material being oriented in at least one direction and at least one other porous material which does not substantially affect the porosity of the microporous material.

3. The layered structure of claim 1 wherein said olefin polymer is polypropylene, block copolymer or copolymers of ethylene and propylene, or other copolymers such as polyethylene, polypropylene and polybutylene copolymers which can be used singularly or in a mixture.

4. The layered structure of claim 1 wherein said processing compound is a hydrocarbon liquid.

5. The layered structure of claim 1 wherein said processing compound is mineral oil or a mixture of mineral oil and mineral spirits.

6. The layered structure of claim 1 wherein said fluorochemical oxazolidinone is a normally solid, water-insoluble, fluoroaliphatic radical-containing 2-oxazolidinone compound which has one or more 2-oxazolidinone moieties, at least one of which has a monovalent fluoroaliphatic radical containing at least 3 fully fluorinated terminal carbon atoms bonded to the 5-position carbon atom thereof by an organic linking group.

7. The layered structure of claim 1 wherein the fluorochemical oxazolidinone is blended with the polyolefin and processing compound at extrusion and comprises about 0.3 to 7 weight percent of the material.

8. The layered structure of claim 1 wherein the fluorochemical oxazolidinone is blended with the polyolefin and processing compound at extrusion and comprises about 1 to 2 weight percent of the material.

9. The layered structure of the claim 6 wherein said fluorochemical oxazolidinone can be represented by the formula

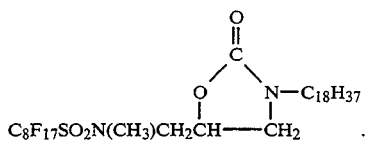

10. The layered structure of claim 1 wherein the fluorochemical oxazolidinone is topically applied to liquid repellent, moisture vapor permeable, microporous membrane material at a rate of at least 5 percent by weight based on the weight of the material.

11. The layered structure of claim 1 wherein said moisture vapor transmission rate is at least 700 g/m2/24 hours.

12. The layered structure of claim 1 wherein said material can be heat sealed to form a bond strength of at least 0.1 kg/cm width.

13. The laminated structure of claim 2 wherein said olefin polymer is polypropylene, block copolymers or copolymers of ethylene and propylene, or other copolymers such as polyethylene, polypropylene and polybutylene copolymers which can be used singularly or in a mixture.

14. The laminated structure of claim 2 wherein said processing compound is a hydrocarbon liquid.

15. The laminated structure of claim 2 wherein said processing compound is mineral oil or a mixture of mineral oil and mineral spirits.

16. The laminated structure of claim 2 wherein said fluorochemical oxazolidinone is a normally solid, water-insoluble, fluoroaliphatic radical-containing 2-oxazolidinone compound which has one or more 2-oxazolidinone moieties, at least one of which has a monovalent fluoroaliphatic radical containing at least 3 fully fluorinated terminal carbon atoms bonded to the 5-position carbon atom thereof by an organic linking group.

17. The laminated structure of claim 2 wherein the fluorochemical oxazolidinone is blended with the polyolefin and processing compound at extrusion and comprises about 0.3 to 7 weight percent of the material.

18. The laminated structure of claim 2 wherein the fluorochemical oxazolidinone is blended with the polyolefin and processing compound at extrusion and comprises about 1 to 2 weight of the material.

19. The laminated structure of claim 16 wherein said fluorochemical oxazolidinone can be represented by the formula

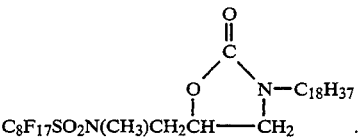

20. The laminated structure of claim 2 wherein the fluorochemical oxazolidinone is topically applied to liquid repellent, moisture vapor permeable, microporous membrane material at a rate of at least 5 percent by weight based on the weight of the material.

21. The laminated structure of claim 2 wherein said moisture vapor transmission rate is at least 700 g/m2/24 hours.

22. The laminated structure of claim 2 wherein said material can be heat sealed to form a bond strength of at least 0.1 kg/cm width.

* * * * *

UNITED STATES PATENT AND TRADEMARK OFFICE
CERTIFICATE OF CORRECTION

PATENT NO. : 5,352,513
DATED : October 4, 1994
INVENTOR(S) : James S. Mrozinski and Harold J. Seppala It is certified that error appears in the above-indentified patent and that said Letters Patent is hereby corrected as shown below:

| | |
|---|---|
| Col. 10, line 4 | "Me.)" should read -- MA) -- |
| Col. 10, line 26 | "(Pp)" should read -- (PP) -- |
| Col. 13, line 56 | "[$CSF_{17}SO_2N(CH_2CH_3)C_2H_4O]_3 PO$, " should read -- [$C_8F_{17}SO_2N(CH_2CH_3)C_2H_4O]_3 PO$, -- |
| Col. 14, line 5 | "polypher" should read -- polymer -- |
| Col. 14, line 34 | "Pp" should read -- PP -- |
| Col. 16, line 46 | "weight of" should read -- weight percent of -- |

Signed and Sealed this

Seventh Day of March, 1995

Attest:

BRUCE LEHMAN

Attesting Officer

Commissioner of Patents and Trademarks